United States Patent
Nagai et al.

(10) Patent No.: US 10,273,532 B2
(45) Date of Patent: Apr. 30, 2019

(54) NUCLEIC ACID AMPLIFICATION METHOD

(75) Inventors: Hidenori Nagai, Ikeda (JP); Yusuke Fuchiwaki, Takamatsu (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 868 days.

(21) Appl. No.: 14/384,135

(22) PCT Filed: Mar. 9, 2012

(86) PCT No.: PCT/JP2012/056079
§ 371 (c)(1),
(2), (4) Date: Sep. 9, 2014

(87) PCT Pub. No.: WO2013/132645
PCT Pub. Date: Sep. 12, 2013

(65) Prior Publication Data
US 2015/0031087 A1    Jan. 29, 2015

(51) Int. Cl.
*C12Q 1/68*    (2018.01)
*C12P 19/34*   (2006.01)
(Continued)

(52) U.S. Cl.
CPC ........... *C12Q 1/686* (2013.01); *C12Q 1/6848* (2013.01)

(58) Field of Classification Search
None
See application file for complete search history.

(56) References Cited

U.S. PATENT DOCUMENTS 6,180,372 B1   1/2001 Franzen
6,960,437 B2  11/2005 Enzelberger et al.
(Continued)

FOREIGN PATENT DOCUMENTS

JP    3041423 B1    3/2000
JP    2001-521622 A 11/2001
(Continued)

OTHER PUBLICATIONS

English translation of Nagai et al. (JP2011-200193 published Oct. 13, 2011), obtained from https://dossier.j-platpat.inpit.go.jp/trt/all/odset/ODSET_GM801_TextTopaction on Nov 21, 2016.*
Abstract of Nagai et al. (JP2011-200193 published Oct. 13, 2011), obtained from East Patent and PGPUB database on Nov. 21, 2016.*
Sugumar D, Ismail A, Ravichandran M, Aziah I, Kong LX. Amplification of SPPS150 and *Salmonella typhi* DNA with a high throughput oscillating flow polymerase chain reaction device. Biomicrofluidics. May 3, 2010; 4(2) pp. 1-12.*
(Continued)

*Primary Examiner* — Young J Kim
(74) *Attorney, Agent, or Firm* — Leydig, Voit & Mayer, Ltd.

(57) ABSTRACT

The invention provides an ultra-rapid nucleic acid amplification method performed in a flow channel. Specifically, the invention provides a nucleic acid amplification method for performing a PCR reaction by supplying a PCR sample solution to a nucleic acid amplification device comprising a serpentine channel adapted to perform at least one PCR cycle, the nucleic acid amplification device comprising a DNA denaturation temperature zone corresponding to the curved portions at one side, an annealing temperature zone corresponding to the curved portions at the other side, and an extension temperature zone positioned between the annealing and DNA denaturation temperature zones, wherein the PCR sample solution is introduced in the form of sample plugs separated by gas into the serpentine channel using a pump, the sample solution being supplied into the channel in a state such that the solution is separated by gas into a segment corresponding to one PCR cycle or smaller segments.

8 Claims, 6 Drawing Sheets

(51) Int. Cl.
*C12Q 1/686* (2018.01)
*C12Q 1/6848* (2018.01)

(56) References Cited

U.S. PATENT DOCUMENTS

| | | | |
|---|---|---|---|
| 2005/0202489 A1* | 9/2005 | Cho | B01L 3/5027 435/6.12 |
| 2007/0111303 A1* | 5/2007 | Inoue | B01L 3/0268 435/287.2 |

FOREIGN PATENT DOCUMENTS

| | | | |
|---|---|---|---|
| JP | 2007-520229 A | 7/2007 | |
| JP | 2008-529555 A | 8/2008 | |
| JP | 2011-200193 | * 10/2011 | C12N 15/09 |
| WO | WO 1998/045481 A1 | 10/1998 | |
| WO | WO 1999/064848 A1 | 12/1999 | |
| WO | WO 2002/083952 A1 | 10/2002 | |
| WO | WO 2005/075683 A1 | 8/2005 | |
| WO | WO 2006/089192 A2 | 8/2006 | |
| WO | WO 2006/124458 A2 | 11/2006 | |

OTHER PUBLICATIONS

Zhang C, Xing D. Microfluidic gradient PCR (MG-PCR): a new method for microfluidic DNA amplification. Biomed Microdevices. Feb. 2010; 12(1):1-12.*

Fuchiwaki Y, Saito M, Wakida S, Tamiya E, Nagai H. A practical liquid plug flow-through polymerase chain-reaction system based on a heat-resistant resin chip. Anal Sci. 2011; 27(3):225-30.*

Zhang, Chunsun, Jinliang Xu, Jianqin Wang, and Hanping Wang. Continuous-flow Polymerase Chain Reaction Microfluidics by Using Spiral Capillary Channel Embedded on Copper. 2007, Analytical letters 40(3): 497-511.*

Malo et al., "Targeted gene walking by low stringency polymerase chain reaction: Assignment of a putative human brain sodium channel gene (SCN3A) to chromosome 2q24-31," PNAS, USA, April, vol. 91, pp. 2975-2979 (Year: 1994).*

Fuchiwaki et al., *Biosensors and Bioelectronics*, 27(1): 88-94 (2011).

Fuchiwaki et al., "Ultra-Fast and Highly-Efficient Flow-Through PCT Microfluidics Using Vapor Pressure and Its Application to Rapid Field Detection," *14th International Conference on Miniaturized Systems for Chemistry and Life Science*, pp. 148-150 (Oct. 3-7, 2010).

Nagai et al., "Development of Ultra-Rapid Gene Detection System", *Research Catalog*, p. 86, item L-21 (2010).

Nagai et al., "Development of Ultra-Rapid Gene Detection System Using Segment-Flow PCR", *The Society for Chemistry and Micro-Nano Systems*, p. 77, item PC15 (Jun. 10, 2011).

Kopp et al., *Science*, 280: 1046-1048 (1998).

Lagally et al., *Analytical Chemistry*, 73(3): 565-570 (2001).

Nagai et al., *Analytical Chemistry*, 73(5): 1043-1047 (2001).

Japanese Patent Office, International Search Report in International Patent Application No. PCT/JP2012/056079 (dated Apr. 3, 2012).

* cited by examiner

NUCLEIC ACID AMPLIFICATION METHOD

CROSS-REFERENCE TO RELATED APPLICATIONS

This patent application is the U.S. national phase of International Patent Application No. PCT/JP2012/056079, filed Mar. 9, 2012, which is incorporated by reference in its entirety herein.

TECHNICAL FIELD

The present invention relates to a method for ultra-rapid nucleic acid amplification in a serpentine channel. More specifically, the present invention relates to a method that provides flow conditions and a flow channel design for accurately controlling temperature using a continuous-flow microfluidic system, and performs an ultra-rapid polymerase chain reaction (PCR).

BACKGROUND ART

Genetic testing has been central to various fields, such as drug development, forensic medicine, clinical tests, and identification of agricultural products or pathogenic microorganisms. Genetic testing serves as a ubiquitous technique for, for example, disease diagnosis and prognosis, marker selection, safety evaluation of food products and environments, and identification of crime scene evidence. Genetic testing is well known for being used in tests for confirming infectious diseases, such as foot-and-mouth disease and new pandemic influenza, which became issues last year. In 2007, the Health Insurance Bureau of the Ministry of Health, Labour and Welfare of Japan approved oncogene testing to be covered by insurance. Since then, clinical test-related companies have announced the commercialization of apparatus or kits for genetic testing, and genetic testing is now gaining momentum in medical treatment as well.

One of the most powerful and basic techniques for detecting a small amount of nucleic acid, i.e., a gene, in a highly sensitive manner is to exponentially replicate some or all of the nucleic acid sequence, and analyze the amplification product.

The polymerase chain reaction (PCR) is a powerful technique used to selectively amplify a certain specific region of DNA. PCR can generate millions of copies of DNA fragments of a target DNA sequence from a single template DNA. PCR is performed by repeating a three-phase temperature condition, which is called a thermal cycle. Specifically, the following individual reactions are successively repeated: denaturation of DNA into single-stranded DNA; annealing of primers to the denatured single-stranded DNA; and extension of the primers by a thermostable DNA polymerase. This cycle is repeated until a number of copies sufficient for analysis is obtained. In principle, each cycle of PCR can double the number of copies. In practice, as thermal cycling continues, the buildup of amplified DNA products eventually ceases, since the reaction reagent concentration decreases to a level lower than that required for the reaction to proceed. For the general details of PCR, see "Clinical Applications of PCR," Dennis Lo (ed.), Humana Press (Totowa, N.J.) (1998), and "PCR Protocols: A Guide to Methods and Applications," M. A. Innis et al. (ed.), Academic Press Inc. (San Diego, Calif.) (1990).

The PCR method is a powerful technique used to exponentially amplify genes by thermal cycling. However, in a generally used thermal cycling device used in PCR, the temperature control is slow due to the huge thermal capacity of the aluminum block heater; thus, the PCR procedure requires 1 to 2 hours for 30 to 40 cycles. Even when the latest genetic testing device is used, the analysis requires a total of several hours. Therefore, speeding up the PCR procedure has been a major object since this technique was introduced.

To achieve the above object, a microfluidic device related to DNA amplification by PCR has also been developed. Thermal cycling of the sample is usually accomplished by one of three methods.

In the first method, the sample solution is loaded into the device, and the temperature cycling is performed over time while the solution is maintained at the same position. This is much like a conventional PCR instrument (Non-patent Documents 1 and 2, and Patent Document 1). Although the purpose of this method is to speed up thermal cycling by reducing the sample amount to reduce the thermal capacity, the reduction in the thermal capacity of the heater or chamber itself is limited, and at least about 30 seconds is required per cycle to sufficiently perform the amplification reaction; therefore, even with the use of the highest-speed device, 15 minutes or longer must be spent to complete the PCR reaction.

In the second method, a plurality of temperature zones spatially apart from each other are connected through a micro-flow channel, and the sample solution is heated while moving back and forth from one zone to another in the same flow channel, in such a manner that the sample stays in each temperature zone for a predetermined time. This method is excellent in that thermal cycling can be performed by arbitrarily setting the time for each temperature zone. However, a number of integrated valves and pumps are used to introduce the sample and pump it through the temperature zones in a rotary fashion; thus, downsizing the device is difficult (Patent Document 3).

In the third method, called continuous-flow PCR, the sample solution is continuously fed in, without being stopped, to move through a plurality of temperature zones spatially separated from each other via a micro-flow channel, similar to the second method. Of the continuous-flow PCR methods, one that is attracting attention is a system for rapidly controlling the sample temperature by allowing the sample to flow through a serpentine channel on three heaters, each having a certain controlled temperature (Non-patent Document 3). In this system, it is not necessary to change the temperatures of external devices such as containers and heaters. Therefore, in theory, this system is expected to achieve the temperature control at the highest speed. In view of this, developments have been made to realize commercialization of this system. However, this system has not yet been put to practical use, as it suffers from problems such as the flow frequently being stopped due to air bubbles randomly formed at a heating zone. Specifically, in continuous-flow PCR, a PCR sample is continuously introduced so as to fill the entire micro-flow channel through 2 to 3 individual temperature zones. However, such a continuous flow requires a large amount of PCR sample, and complicated controls. Further, air bubbles are easily formed at the denaturation temperature zone at 95° C., frequently causing the disturbance and stopping of the flow. Moreover, the sample solution passes through several meters of a microtube or micro-flow channel to repeatedly move through each temperature zone about 30 to 40 times; thus, the fluid resistance becomes large as the flow speed becomes slow, preventing efficient and rapid temperature control from being achieved. As a result, about 1 hour is required to complete continuous-flow PCR; even with the use of a high-speed system, 15 minutes or more is required.

The market for genetic testing using PCR/real-time PCR devices has been growing stably. In particular, genetic testing for infectious diseases, such as viral hepatitis, sexually transmitted diseases, and influenza, has become more prevalent domestically. Further, the usefulness of genetic testing in cancer treatment has become clear. For example, an EGFR gene mutation can be used, for example, as an indication for application of the anticancer drug Iressa. Based on this fact, genetic testing in relation to EGFR gene, K-RAS gene, EWS/Fli-1 gene, TLS-CHOP gene, SVT-SSX gene, and c-kit gene in lung cancer, pancreatic cancer, and the like, has recently become insurance-covered.

Under current conditions, a sample is transported to a laboratory or an analytical center to perform genetic testing. However, if a high-speed genetic testing system, which can be quickly used on-site, is available, a plan of treatment or countermeasure can be determined instantly. Such a system can thus be considered a ground-breaking technique to use in place of currently available genetic testing devices. In particular, to prevent pandemics such as foot-and-mouth disease and highly pathogenic avian influenza from occurring, important factors are a quick and accurate decision on-site, as well as prevention of a secondary infection associated with migration. Therefore, there is a great need for a high-speed genetic testing system. In particular, a high-speed and simple genetic testing technique that can be performed at a low cost is required to achieve realization of services for promptly performing genetic testing at a clinical location or at the location of an infectious disease onset.

However, a quick and simple PCR that can be performed on-site is not available with current technology, and a method for ultra-rapidly performing amplification has been in demand.

CITATION LIST

Patent Documents

Patent Document 1: Japanese Patent No. 3041423
Patent Document 2: U.S. Pat. No. 6,960,437
Patent Document 3: WO 2006/124458

Non-Patent Documents

Non-patent Document 1: Lagally et al., Anal Chem 73: 565-570 (2001)
Non-patent Document 2: Nagai et al., Anal Chem 73: 1043-1047 (2001)
Non-patent Document 3: Kopp et al., Science 280: 1046-1048 (1998)

SUMMARY OF INVENTION

Technical Problem

An object of the present invention is to provide a method for ultra-rapid nucleic acid amplification in a flow channel.

Solution to Problem

To achieve the above object, the present inventors employed segmented flow of a sample solution that is introduced in a size of several microliters and that is continuously pushed by air, rather than a continuous flow of a sample solution that is introduced to fill the entire micro-tube or micro-flow channel, as in known continuous-flow PCR. In this manner, the present inventors succeeded in eliminating the effect caused by air-bubble formation, accelerating annealing by using high-speed internal convection of the sample solution, and achieving high flow speed by reducing pressure loss.

The present invention uses vapor pressure changes produced during successive heating while a sample solution is flowing. The sample solution is thereby allowed to move slowly in the temperature-increasing direction, and quickly in the temperature-decreasing direction. In this manner, the present invention makes it possible to ensure a long extension reaction, and suppress extension of by-products at a transition temperature; the present invention is thus considered a high-speed and efficient PCR technique.

In the thermal cycle using the above flow channel, in particular, the control of accurate change in the temperature of a sample solution within a short period of time is indispensable. Therefore, an object of the present invention is to set flow conditions and a flow channel design by using a micro-flow channel in such a manner that the temperature of the PCR sample in the form of segmented flow is accurately controlled so as to provide a method for ultra-rapid nucleic acid amplification in the flow channel.

The present invention provides the following nucleic acid amplification method.

Item 1. A nucleic acid amplification method for performing a PCR reaction by supplying a PCR sample solution to a nucleic acid amplification device comprising a serpentine channel adapted to perform at least one PCR cycle, the nucleic acid amplification device comprising:

a DNA denaturation temperature zone corresponding to the curved portions at one side;

an annealing temperature zone corresponding to the curved portions at the other side; and an extension temperature zone positioned between the annealing temperature zone and the DNA denaturation temperature zone, wherein the PCR sample solution is introduced in the form of sample plugs separated by gas into the serpentine channel using a pump, the sample solution being supplied into the serpentine channel in a state such that the solution is separated by gas into a segment corresponding to one PCR cycle or smaller segments.

Item 2. The nucleic acid amplification method according to Item 1, wherein the method uses a temperature control method, in which a difference between vapor pressure produced at an interface between the front of each sample plug and gas, and vapor pressure produced at an interface between the back of each sample plug and gas is used to reduce the speed of the sample plug flowing from the annealing temperature zone to the DNA denaturation temperature zone in the heating process to ensure time for an enzymatic extension reaction in the extension temperature zone, and to increase the speed of the sample plug flowing from the DNA denaturation temperature zone to the annealing temperature zone in the cooling process, so that the sample solution passes through the cooling process quicker than through the heating process.

Item 3. The nucleic acid amplification method according to Item 1 or 2, wherein the PCR sample solution is supplied at a volume equal to or less than that of a straight-line portion of the serpentine channel.

Item 4. The nucleic acid amplification method according to any one of Items 1 to 3, wherein the method uses a thin-membrane film for monitoring the temperature of the solution within the flow channel in a chip.

Item 5. The nucleic acid amplification method of any one of Items 1 to 4, wherein the temperature control method for the sample plug comprises at least one of the temperature control methods below:

(i) a method in which the temperature of an annealing heater for reducing temperature is cooled to 40° C. or less;

(ii) a method in which parallelly positioned flow paths of the serpentine channel have intervals of 200 μm or more to maintain thermal capacity; and (iii) a method in which the cross-sectional aspect ratio of the flow channel is set to ⅛ or more and less than 1 to prevent air bubbles from being formed and to stabilize the flow.

Advantageous Effects of Invention

There is a demand for the realization of a system capable of examining the presence or absence of a gene from a minimal amount of a biological sample collected in medical practice, as in genetic testing with high sensitivity. Here, microfluidic devices have advantageous characteristic features in that they use minimized analytical volume and achieve maximized heat transfer efficiency with an increase in the surface area relative to the volume. The use of these features is necessary to establish a technique for high-speed minimal-volume gene amplification. Unlike the existing method in gene-amplification technique, i.e., PCR, the present invention uses the morphology (form) of sample plugs separated by air to use the vapor pressure of the sample solution itself. By using vapor pressure produced at the interface between the front of the sample plug and air, and vapor pressure produced at the interface between the back of the sample plug and air, the present invention can achieve both high speed and excellent efficiency, which have been unsolved problems of known continuous-flow PCR using a flat-plate type microfluidic device. The present invention thus has features such that it requires no additional special external device and contributes to minimization of the sample volume and speeding up of a continuous-flow PCR, with maximum use of the advantages of the microfluidic device.

BRIEF DESCRIPTION OF DRAWINGS

In FIG. 2, a temperature controller 1 (about 95° C.) is a heater block 7 for DNA denaturation, a temperature controller 2 (about 72° C.) is a heater block 6 for extension reaction, a temperature controller 3 (about 55° C.) is a heater block 5 for annealing, and sample solutions 1 to 3 are sample plugs (samples) 8.

DESCRIPTION OF EMBODIMENTS

The present invention relates to a nucleic acid amplification method using a very high-speed polymerase chain reaction (PCR) in a micro-flow channel, which repeatedly passes through a plurality of temperature zones in a meandering manner. More specifically, an object of the present invention is to provide a method using a micro-flow channel in a flat-plate type microfluidic system for continuous-flow PCR, provided with a flow channel design for accurately controlling the temperature of a PCR sample flowing as sample plugs separated by air by and appropriately set flow conditions thereby performing ultra-rapid nucleic acid amplification in the flow channel.

In this specification, a plurality of temperature zones indicates a DNA denaturation temperature zone, an annealing temperature zone, and an extension temperature zone. It is possible for these three temperature zones to be clearly distinguished from each other by a heating device (heater) or a cooling device. It is also possible for the adjacent temperature zones (the DNA denaturation temperature zone and the extension temperature zone, or the extension temperature zone and the annealing temperature zone) to not have a clear boundary. In particular, the extension temperature zone and the annealing temperature zone may be one integrated temperature zone in appearance. Even in this case, in this specification, a portion having a higher temperature is referred to as an extension temperature zone, while a portion having a lower temperature is referred to as an annealing temperature zone.

All of the techniques and scientific terms used in this specification have the same meanings as those generally understood by a person skilled in the art in the technical field relevant to the present invention, unless otherwise noted. The present invention is described below in detail with reference to embodiments. However, the present invention is not limited to these embodiments, and any method and material similar or equivalent to those described in this specification may be used to practice the invention. The following describes preferable materials and methods.

Figure 1:
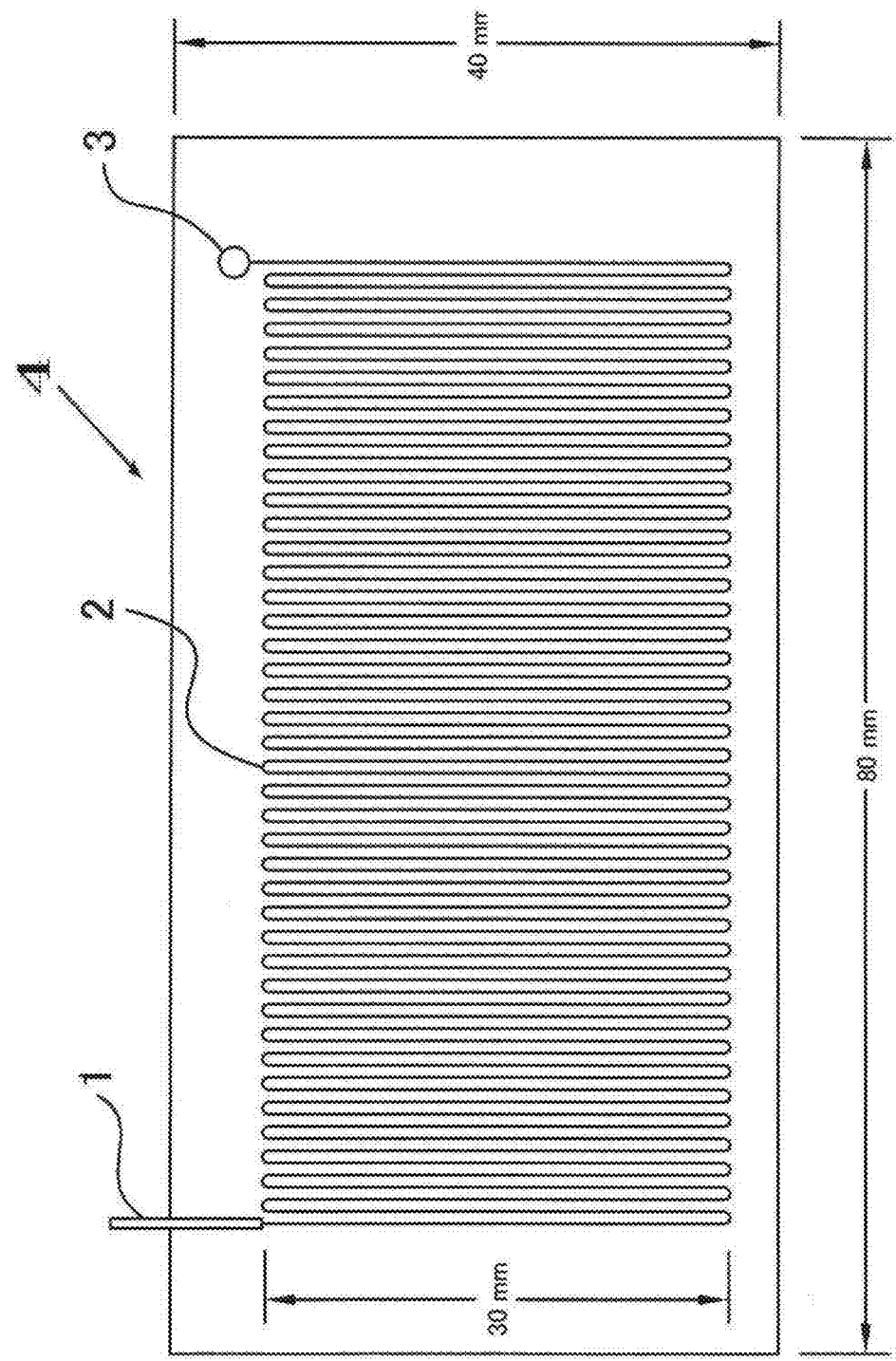
FIG. 1 shows a continuous-flow PCR microfluidic device 4.

FIG. 1 shows a schematic diagram of a continuous-flow PCR microfluidic device 4 used to practice the present invention. The device includes a PCR reagent inlet 1, a serpentine channel 2, and a reservoir 3 for storing a liquid after PCR reaction. One PCR cycle may be performed using one unit comprising a pair of curved portions at both sides (a high-temperature denaturation zone (corresponding to the DNA denaturation temperature zone) and a low-temperature annealing zone) and two straight-line portions, each connecting the curved portions. The high-temperature denaturation zone corresponds to the "DNA denaturation temperature zone," the low-temperature annealing zone corresponds to the "annealing temperature zone," and the two straight-line portions connecting the curved portions correspond to the "extension temperature zone." In the microfluidic device used in the present invention, a serpentine channel 3 may be formed of one unit described above, or may be formed of a large number of these units connected to each other. When a single PCR sample solution moves forward through the serpentine channel, one cycle or a large number of cycles of PCR reaction is performed according to the number of units of the serpentine channel, and a required number of PCR products are produced and discharged to a reservoir.

The continuous-flow PCR microfluidic device 4 of FIG. 1 is produced by cutting, for example, a flat cyclo olefin resin (COP) plate (length: 76 mm, width: 52 mm; and thickness: 2 mm) into the shape of a flow channel designed by CAD, using an NC machine. The material of the microfluidic device may be an acrylic-based resin, a polycarbonate-based resin, a polystyrene resin, a fluorine-based resin, and the like, other than a polyolefin resin such as COP. In the formation of the flow channel, a method available for microprocessing of resin, such as injection molding, nanoimprinting, or soft lithography, may be used, in addition to a machinery processing machine such as an NC machine. When a cutting process is employed, an end mill for resin (diameter: 200 μm) is used to cut a material into a micro-flow channel in a semi-circular or rectangular cross-sectional shape having a width of 10 to 1000 μm and a depth of 10 to 1000 μm, and preferably a width of 400 μm and a depth of 500 μm. In the practice of the present invention, a straight groove having a width and depth of 0.65 mm was formed by cutting from the end at the sample solution injection side of the micro-flow channel to the end of a COP plate. The end of the outlet side had a shape to which a cylindrical reservoir having a diameter of 2 mm was connected. A sufficient length of a metal tube having an outer diameter of 0.65 mm was inserted into the groove from the injection side in such a manner that the tube would not naturally come out, and an adhesive agent was applied only to the peripheral portion of the metal tube to prevent solution leakage. Thereafter, the entire serpentine channel surface including the metal tube portion was covered with a microplate sealing tape (9795 from 3M) coated with a pressure-sensitive adhesive agent, thereby producing a continuous-flow PCR microfluidic device having a built-in PCR sample injection tube. The PCR sample injection tube is not limited to a tube made of metal, and may be made of a resin, such as a silicone. It is also possible for the tube to be made of a rubber material, a glass material, or the like. For covering, a different sealing adhesive agent or a tape agent may be used. Alternatively, thermal sealing may be employed using a resin material. The sealing tape at the portion covering the reservoir at the outlet side of the micro-flow channel was cut off.

Figure 2:
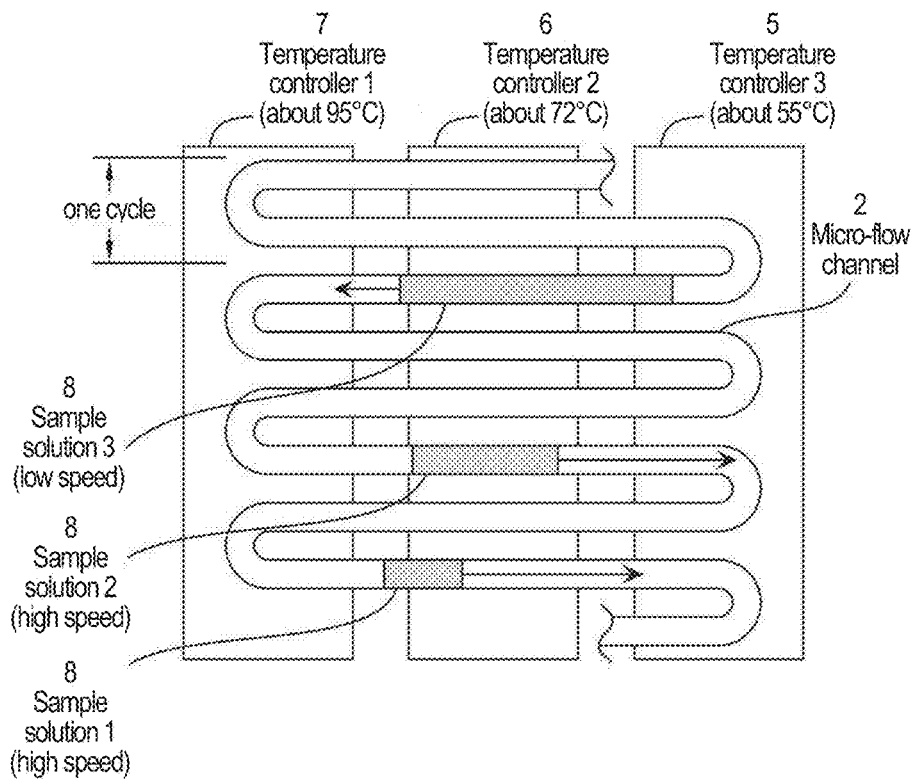
FIG. 2 shows a method for controlling the temperature of each zone on the serpentine channel to perform thermal cycles in the continuous-flow PCR microfluidic device of FIG. 1.

As shown in FIG. 2, three heater blocks 5, 6, and 7 (the temperature controllers 3, 2, and 1, respectively), each having a length of 150 mm, a width of 15 mm, and a height of 10 mm, and a built-in heater, were disposed in parallel at intervals of about 0.5 to 1 mm. The produced continuous-flow PCR microfluidic device was disposed on these heaters so as to be in contact with them, allowing the temperatures on the three contact zones to be individually and locally controlled. Each heater block has a property in which the surface of the heater block can be uniformly heated to 120° C. or more. By attaching a Peltier device to the bottom, the heaters were given the function to cool the temperature to 5° C. or less. The temperature of each of the aluminum blocks 5, 6, and 7 is PID-controlled based on the temperature sensor provided inside each block, and is thus constantly and uniformly maintained with the heater or Peltier device. The temperatures of the aluminum blocks 5, 6, and 7 shown in FIG. 2 were individually set so as to allow the sample solution to have a temperature of 95° C., 72° C., or 55° C., which is required for the denaturation, extension, or annealing of PCR. Once the temperature of each aluminum block is set, it is not necessary to change the temperatures, as long as a continuous-flow PCR is performed under the same conditions.

The serpentine channel of the continuous-flow PCR microfluidic device was designed in such a manner that the channel continuously curves at every 30-mm length into the opposite direction while leaving intervals of 10 to 1000 μm, desirably 400 μm, to form a serpentine channel. This serpentine channel was designed so that it intersects perpendicularly with the three heater blocks, and the curved portions of the serpentine channel are in contact with the left-side or right-side heater block for a length of 7 mm. The position of the serpentine channel in contact with the left-side and right-side heater blocks may be suitably adjusted according to the target temperature and control time. In the practice of the present invention, stainless steel structures each having a length of 150 mm, a width of 15 mm, and a thickness of 10 mm, and an in-built temperature sensor were used as heater blocks for continuous-flow PCR. These structures were disposed in line at intervals of 1 to 2 mm. Either of the left-side or right-side structures was allowed to be in contact with a Peltier device so that the temperature thereof could be controlled at room temperature or lower. Further, 40 curved portions were designed to be positioned on each of the left-side and right-side heater blocks among the three heater blocks; in this manner, it was possible to perform a thermal cycle required for PCR 40 times. FIGS. 1 and 2 show an example in which three temperature zones and the serpentine channel capable of performing a thermal cycle 40 times are used. However, it is also possible to design the serpentine channel to perform a single thermal cycle. Providing two temperature zones is also possible.

The number of serpentine channels may be designed to be two or more, although a single (independent) channel is preferable to achieve prompt analysis.

Table 1 below shows the recommended ratio of preferable temperature and time for annealing, extension, and denaturation.

TABLE 1

|  | Annealing (55-59° C.) | Extension (72° C.) | Denaturation (95° C.) |
| --- | --- | --- | --- |
| Recommended Ratio | 2 | 3 | 1 |

The continuous-flow PCR microfluidic device may be designed to satisfy the recommended ratio shown in Table 1 above when the device includes three temperature zones, i.e., a heater block for DNA denaturation, corresponding to the curved portions at one side; a heater block for annealing, corresponding to the curved portions at another side; and a heater block for extension reaction, corresponding to the straight-line portions connecting the curved portions at both sides. When PCR is performed in thermal cycles under two different temperature settings, i.e., using a heater block for DNA denaturation, corresponding to the curved portions at one side, and a heater block capable of performing an extension process, corresponding to the straight-line portions and the curved portions at another side (the extension process is performed at a temperature changed from the annealing temperature to the denaturation temperature), PCR may be performed using a ratio equivalent to the recommended ratio shown in Table 1.

The temperature of each heater block is constantly controlled at a target temperature by PID control. The surface temperature of each heater block or the surface temperature of the continuous-flow PCR microfluidic device is confirmed using a contact or non-contact type temperature sensor, as required. The temperature of each heater block can then be adjusted to a level required for each reaction of PCR, as shown in Table 1. In the practice of the present invention, the temperature of the surface of the continuous-flow PCR microfluidic device, the flowing fluid, or the surface of the continuous-flow PCR microfluidic device portions around the flowing fluid was measured with an infrared camera to adjust the temperature to a target temperature.

A standard real-time PCR kit (a CycleavePCR Core Kit produced by Takara Bio Inc.) was used as a PCR sample solution. A 134 bp DNA sample (positive control) from the kit was used as the target for amplification in PCR, and a PCR reagent was prepared according to the kit instructions. The PCR primers and probes, i.e., the composition and concentration of the reagent, can be changed depending on the type of target gene for detection.

The introduction of the PCR sample was performed using a syringe pump containing gas in a volume equal to or more than the total volume of the continuous-flow PCR microfluidic device and the sample injection tube connected in the middle of the device. 0.1 to 10 µL, desirably 1 to 5 µL, of the PCR sample was sucked, via a silicone tube, into a 1-mL syringe pump filled with air. Thereafter, the pump was connected to the PCR sample injection tube of the chip to introduce the PCR sample. Alternatively, it is also possible to inject the PCR sample in the following manner: a certain amount of the PCR sample is sucked into a Pipetman, the exchange Pipetman tip containing the PCR sample is removed, and one end of the removed tip is inserted into the PCR sample injection tube while the other end is connected to a syringe pump. In the practice of the present invention, 1 to 30 µL from 300 µL or more of the PCR reagent was injected through the PCR sample injection tube of the continuous-flow PCR microfluidic device via a silicone tube having an inner diameter of 0.5 mm, which is connected to a syringe pump (Model 11, produced by Harvard). At this time, 300 µL of air had already been put into the syringe pump to allow the sample solution to finish flowing from the PCR sample injection tube of the continuous-flow PCR microfluidic device to the reservoir at the micro-flow channel outlet. The flow rate of the syringe pump was set at 65 to 225 µL/min, and the sample solution was continuously introduced to be discharged into the reservoir at the end of the outlet of the micro-flow channel. This corresponds to 1 sec/cycle to 10 sec/cycle, in terms of the time required for the sample solution to flow through a channel length that is equivalent to one cycle of continuous-flow PCR. The pump for introducing a PCR sample may be any pump in addition to a syringe pump, as long as it can introduce a minimal amount of a solution. In this manner, as shown in FIG. 2, a method for performing a continuous-flow PCR by introducing a minimal amount of a PCR sample in the form of sample plugs was established. In the present invention, a sample solution was introduced in a size of several microliters, and continuously pushed by air to form a segmented flow. In this manner, the present invention achieves internal high-speed convection of the sample solution and acceleration of a diffusion-controlled annealing reaction. The PCR solution can rapidly pass through the high-temperature zone before the flow becomes unstable due to air bubble formation; this aspect serves as one of the features of the present invention.

A real-time PCR, such as a CycleavePCR core kit produced by Takara Bio Inc., is a technique of confirming and detecting target DNA amplification by simultaneously increasing fluorescence when the target DNA sequence is amplified. In the practice of the present invention, the target DNA amplification was confirmed by directly measuring the fluorescence intensity of the PCR sample after PCR with a SELFOC fluorescence detector placed in the serpentine channel or at the location of the reservoir. Otherwise, the target DNA amplification was confirmed by measuring the fluorescence intensity of the PCR sample after PCR with a fluorescence microreader after the PCR sample was transferred to a microplate.

The continuous-flow PCR microfluidic device that employs the sample plug form is assumed to enable a rapid flow and simple PCR controls; however, an excessively high flow speed may possibly allow the sample solution to pass through each temperature zone before the sample solution temperature reaches the temperature required for PCR. Therefore, in the present invention, to ensure sufficient reaction time for DNA denaturation, annealing, and extension, vapor pressure generated in the micro-flow channel at the interface between the front of each sample plug and gas, and vapor pressure generated at the interface between the back of each sample plug and gas are efficiently used so that the sample plugs pass through each heater block over the time required for each reaction of PCR; this aspect serves as one of the features of the present invention.

Figure 3:
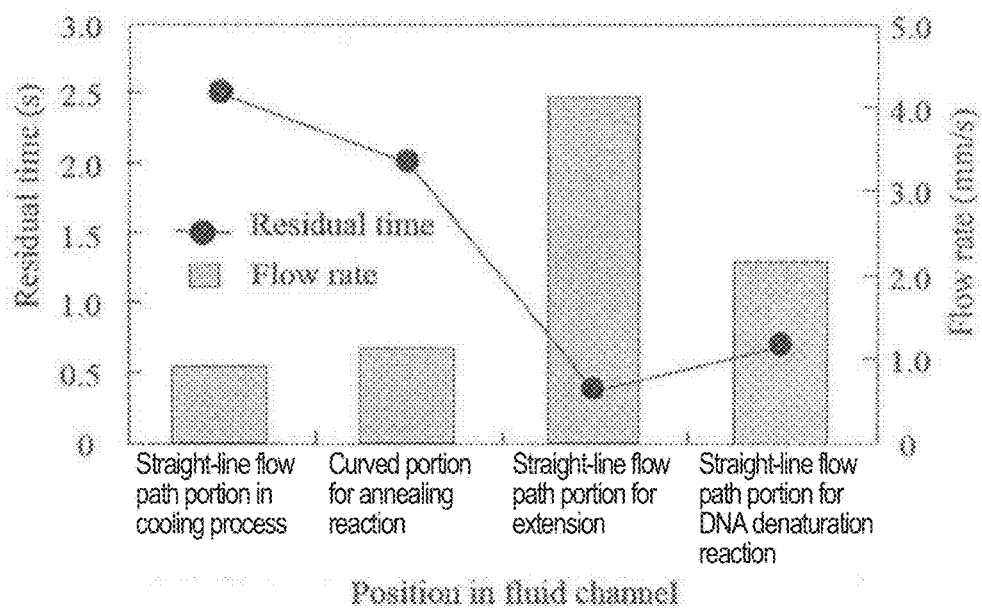
FIG. 3 is a graph showing variations in the flow time and flow rate of sample plugs passing through on the heater blocks of a continuous-flow PCR microfluidic device. These variations are due to the effect of a difference between vapor pressure at the front of each sample plug and vapor pressure at the back of each sample plug.

The time and rate for the sample plug to pass through the heater blocks for each reaction were measured using a video camera. FIG. 3 shows the results. As is clear from the graph of FIG. 3, the transit time was longer in the heating process that involves the extension reaction performed at a position in the parallelly positioned straight-line flow paths of the serpentine channel. This is because the high vapor pressure produced at the heater block for DNA denaturation reaction functions in the direction opposite to the sample plug-flowing direction, reducing the flow speed of the sample plug. In contrast, in the cooling process directed toward annealing from DNA denaturation, the transit time was shortest because the flow speed of the sample plugs was increased due to the same effect of the vapor pressure difference. The denaturation and annealing of PCR proceed very quickly; therefore, the ratio of each reaction time above is equal to that shown in Table 1, and is thus optimum for PCR. This ratio is suitable to effectively ensure the time for the enzymatic extension reaction, which proceeds relatively slowly.

In contrast, in a known continuous-flow PCR, in which a PCR sample is introduced to fill the entire serpentine channel rather than introduced in the form of sample plugs, the flow speed is constant, and the PCR sample travels slowly even from the DNA denaturation temperature zone to the annealing temperature zone in the cooling process, as in other temperature zones. In the annealing process in which the temperature is transiently decreased to the transition temperature at which a primer attaches to a target DNA sequence, it is possible that the primer attaches to a moiety other than the target sequence. This is the cause of the formation of by-products in addition to the target gene sequence. The high-speed cooling realized by the present invention inhibits the formation of by-products and is advantageous in accurate DNA amplification. This aspect serves as one of the features of the present invention.

As shown in FIG. 3, the flow rate varies on each heater block due to the difference between vapor pressure produced at the front of each sample plug and vapor pressure produced at the back of each sample plug. It is therefore necessary to optimize the flow channel design and the temperature to meet the set reaction time and temperature. Accurate DNA amplification is realized only when these conditions are fulfilled. To achieve this, the chip temperature on each temperature zone, including the temperature gradient between the heaters, must be accurately measured. In the practice of the invention, therefore, consideration was given to measuring the temperature of the flowing PCR sample in the micro-flow channel using an infrared camera, the measurement being performed through a polyolefin thin film used as a sealing material. A polyolefin sealing material used in the practice of the present invention had a thickness of 50 µm; it is therefore possible to measure the temperature of each sample plug through the sealing material. The sealing material desirably has a thickness of 0.5 mm or less, or 50 µm or less. The material of the thin film used as a sealing material may be acrylic-based resin, polycarbonate-based resin, polystyrene resin, or fluorine-based resin, in addition to a polyolefin-based resin such as COP. The present invention provides a technique for accurately measuring the temperature of the sample plug inside the serpentine channel through a thin-film sealing material, a cover material, or a film material. This technique serves as one feature of the present invention.

Figure 4:
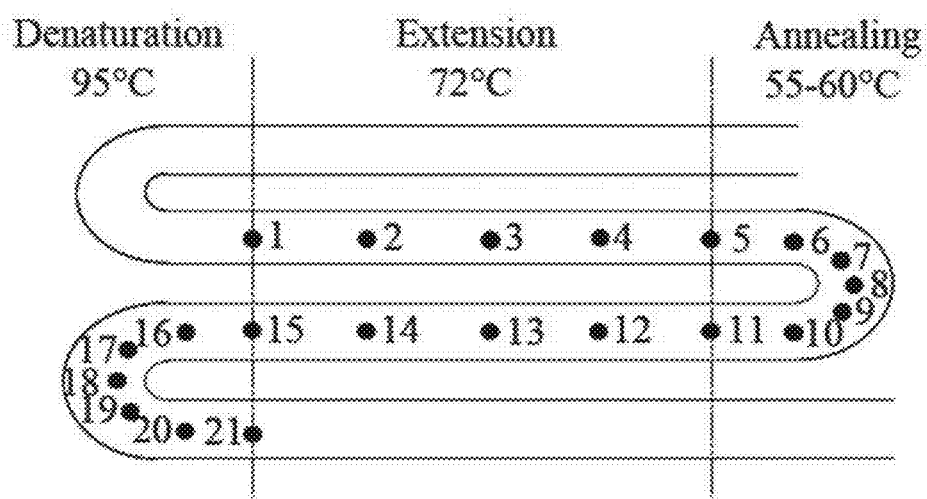
FIG. 4 shows a schematic diagram showing measurement points on the serpentine channel, at which the temperatures of the sample plugs flowing inside the continuous-flow PCR microfluidic device are measured.
Figure 5:
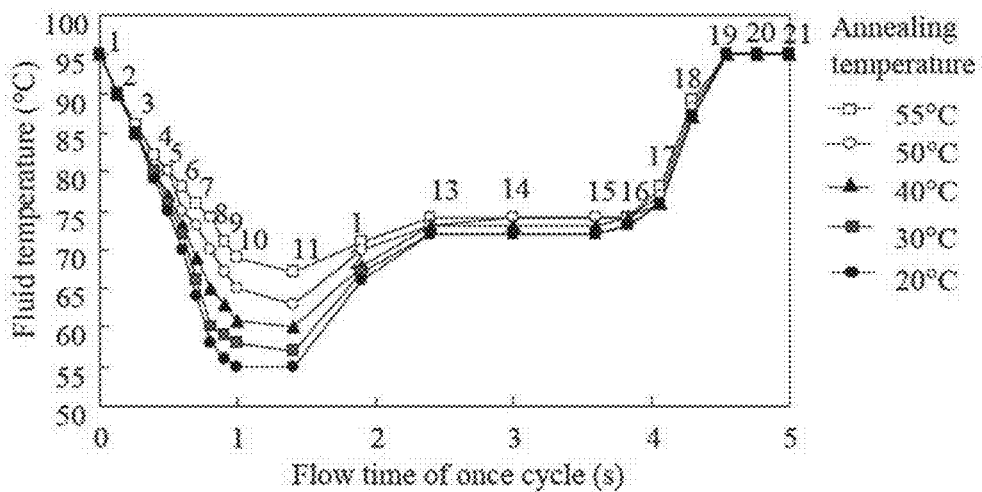
FIG. 5 is a graph showing the measurement results of the temperature at each point shown in FIG. 4.

FIG. 4 shows the measurement points on the serpentine channel. These points are used in the practice of the present invention to actually measure the temperatures of the sample plug passing through inside the continuous-flow PCR microfluidic device. FIG. 5 shows the measurement results of the temperatures at each point of FIG. 4. Importantly, in the rapid temperature control using the sample solution introduced in the form of sample plugs, the time for the cooling process for annealing is significantly short; thus, even if the temperature of the heater block for annealing was set at 55 to 65° C., which is a general annealing temperature, the cooling effect was insufficient and the temperature was not cooled to the set temperature, as shown in FIG. 5. This is because the thermal conductivity of COP, which is a component of the continuous-flow PCR microfluidic device, is several-fold lower than that of water, which is a main component of the sample plug, and a larger temperature difference is thus required for rapid thermal conduction. In view of the above, the temperature of the heater block for annealing was lowered and observed. As shown in FIG. 5, the temperature of the sample plug decreased according to the temperature of the heater block for annealing. The fluorescence intensity after PCR was also compared. As shown in Table 2, the fluorescence intensity was increased when the heater block for annealing had a temperature of 40° C. or less; thereby, DNA amplification was confirmed. In the practice of the present invention, in particular, when the heater block for annealing had a temperature of 20° C., the largest increase in the fluorescence intensity was seen. As is clear from FIG. 5, it is assumed that the sample plug was sufficiently cooled to a temperature required for annealing reaction. In the present invention, to rapidly control the temperature of the sample plug, the temperature of each heater is set to an excessively higher or excessively lower temperature than the general annealing temperature. This aspect serves as one feature of the present invention.

TABLE 2

|  | Temperature of heater block for annealing (° C.) | | | | |
| --- | --- | --- | --- | --- | --- |
|  | 55 | 50 | 40 | 30 | 20 |
| Fluorescence intensity after continuous-flow PCR | 0.29 ± 0.18 | 0.32 ± 0.21 | 1.07 ± 0.56 | 2.77 ± 0.29 | 3.27 ± 0.32 |

Figure 6:
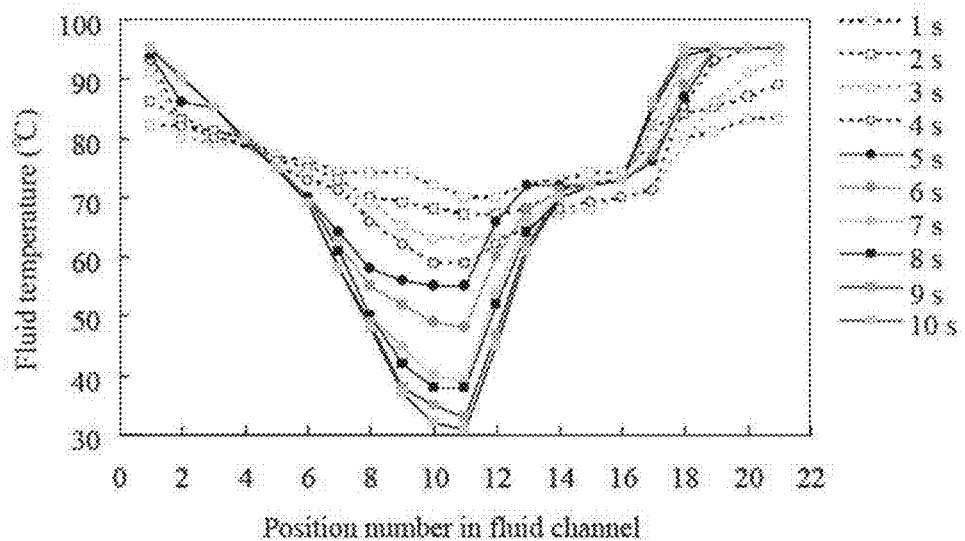
FIG. 6 is a graph showing the measurement results of the temperature at each point shown in FIG. 4 when the time per cycle in the continuous-flow PCR microfluidic device is adjusted to 1 to 10 s.

As described above, the sample plug temperature attained at each temperature zone is influenced by the flow rate. Therefore, the flow rate of the syringe pump was varied and measured at each point shown in FIG. 4. FIG. 6 shows the measurement results of the temperature when the time per cycle was set to 1 to 10 s. When the flow speed was as fast as 1 to 2 s per cycle, the sample plug temperature did not reach the temperature required for PCR at all of the temperature zones. In contrast, when the heater block for annealing had a temperature of 20° C., and when the time per cycle was set to 7 s or more, the sample plug temperature was excessively cooled to 40° C. or less, at which misannealing easily occurs.

In view of the above, the optimization of the temperature of each heat block and the flow rate are important to the temperature control in the continuous-flow PCR using sample plugs. In the practice of the present invention, when the heater block for annealing had a temperature of 20° C., the optimal flow rate was 5 to 6 s per cycle.

Figure 7:
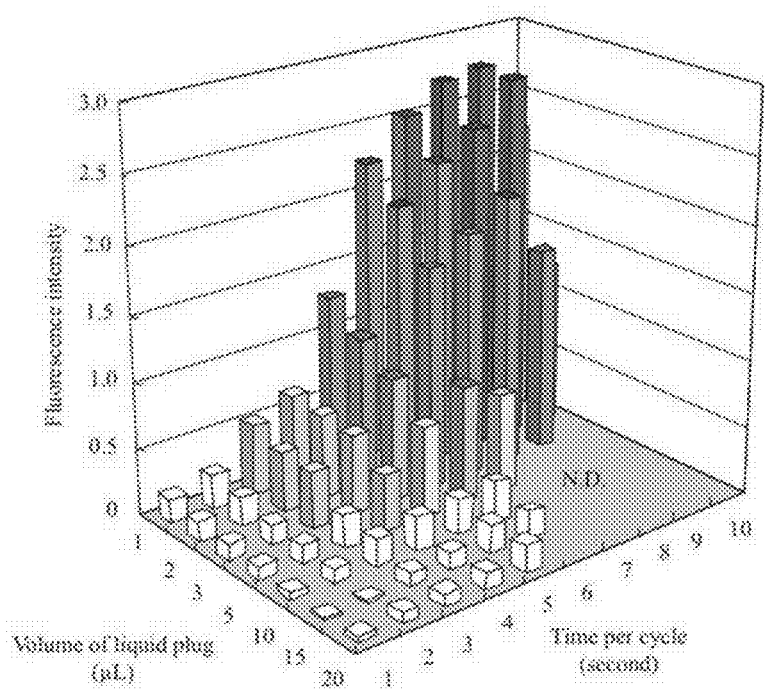
FIG. 7 is a graph showing fluorescence intensity obtained in association with DNA fragment amplification using a real-time PCR kit, when a continuous-flow PCR was performed by using the continuous-flow PCR microfluidic device and by changing the volume and flow speed of reagent plugs in the form of sample plugs.

DNA amplification by PCR was confirmed by collecting the sample solution that arrived at the reservoir, and calculating the variation of the fluorescence intensity before and after the continuous-flow PCR using a fluorescence plate reader (Fluoroskan Ascent produced by Thermo Scientific) adjusted for use with FAM dyes. The results of continuous-flow PCR showed that an increase in the fluorescence intensity, which indicates the amplification of the target DNA fragment, is dependent on the time required per cycle, as shown in FIG. 7. This is because when the time per cycle was increased by decreasing the flow rate, sufficient thermal conduction and reaction time required for each reaction of PCR, such as denaturation, annealing, and extension, were provided.

It is clear from FIG. 7 that when the sample solution is introduced in the form of sample plugs to perform continuous-flow PCR, as in one of the features of the present invention, the efficiency in PCR is improved at more than the expected extent upon decrease in the volume of the sample solution. In the Examples of the present invention, each straight-line flow path of the serpentine channel has a flow length of 30 mm, which is equivalent to a volume of about 5.5 µL. As shown in the Examples, when the amount of reagent solution is 10 µL or more, the length of the sample plug size exceeds the length equivalent to one cycle. The sample plug thus flows at a constant rate without being influenced by a difference between vapor pressure produced at the front of the sample plug and vapor pressure produced at the back of the sample plug. This means that the travelling time at the zone at 72° C. that contributes to the extension reaction and that is located at a position from the zone at 55° C. toward the zone at 95° C. becomes equal to the travelling time at the zone at 72° C. that is located at a position from the zone at 95° C. toward the zone at 55° C. after curving to the opposite direction. However, when the volume of the sample solution is 5.5 µL or less, the size of the sample plug is within the size of the straight-line portion of the serpentine channel. Therefore, in the heating or cooling of the thermal cycle, the gas-liquid interfaces at the upper- and lower-stream sides of the sample plug each individually vary in vapor pressure; i.e., they momentarily vary depending on the position in the serpentine channel. In this manner, in the extension reaction process at a position from the zone at 55° C. toward the zone at 95° C., the vapor pressure at the gas-liquid interface at the upstream side is increased, compared to that of the downstream side, thereby generating the power that goes against the flowing direction; the sample plug thereby moved at a low speed, as shown in FIG. 3. In contrast, in the micro-flow channel at a position from the zone at 95° C. toward the zone at 55° C., the vapor pressure at the gas-liquid interface at the downstream side is increased, thereby accelerating the flow; the sample plug thereby moved at a speed 2- to 3-fold higher than the above.

The increases in the fluorescence intensity obtained after PCR cycles were compared between the case where the sample solution was used at a volume of 5 µL or less and the case where the sample solution was used at a volume of 10 µL or less. As is clear from FIG. 7, the former case achieved a 2- to 6-fold higher efficiency, even at the same average flow rate. As such, the use of the vapor pressure difference at both ends of the sample plug ensures a long time for the extension reaction at 72° C. following the zone at 55° C. This is advantageous for PCR. In contrast, the sample plug rapidly passes through the extension zone (72° C.) at a position from the denaturation zone (95° C.) back toward the annealing zone (55° C.). The extension zone (72° C.) here is unnecessary for PCR but is provided due to the restriction of the design of the serpentine channel. In this manner, ideal thermal cycles are achieved while generating no by-products, and continuous-flow PCR with both high speed and high efficiency is thereby achieved. Therefore, as one preferable feature of the present invention, a sample plug is supplied at a volume less than the volume equivalent to each of the straight-line portions of the serpentine channel.

Here, the shape of the serpentine channel of the continuous-flow PCR microfluidic device also exerts influence on the temperature control of the sample plug. Thus, in the practice of the present invention, the influence on the target DNA amplification was evaluated in terms of the case where the depth of the micro-flow channel was changed to vary the cross-sectional aspect ratio (ratio of the flow channel depth to the channel width), and the case where the intervals between the parallelly positioned straight-line flow paths of the flow channel was changed.

Figure 8:
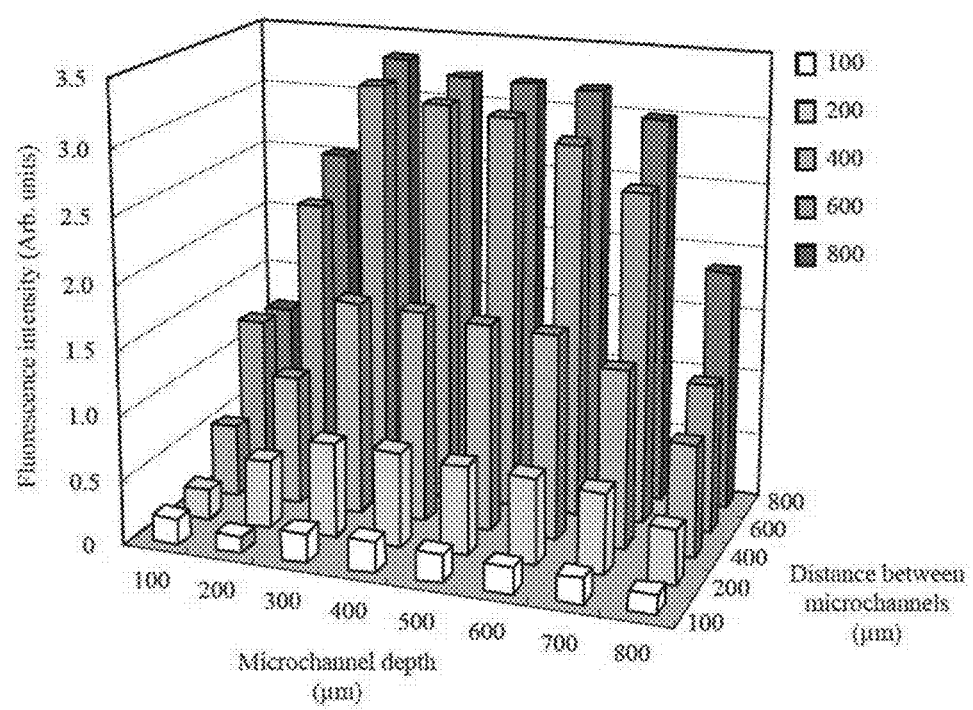
FIG. 8 is a graph showing fluorescence intensity obtained in association with DNA fragment amplification using a real-time PCR kit, when a continuous-flow PCR was performed by using the continuous-flow PCR microfluidic device and by changing the depth of the flow path of the serpentine channel and the intervals between the parallelly positioned straight-line flow paths of the flow channel.

The flow channel depth was varied while the channel width was fixed at 800 µm to analyze the change in the amount of fluorescence. As shown in FIG. 8, it is desirable that the aspect ratio be set at a value greater than ⅛ and less than 1. When the flow channel depth was 100 µm, which is equivalent to ⅛, the amount of fluorescence in real-time PCR showed a reduced increase. This is because the flow channel was too shallow, and the heat was excessively transferred at the position on the heater block for DNA denaturation reaction, causing effects such as sample plug transpiration. In contrast, when the flow channel depth was 800 µm, which is equivalent to the aspect ratio of 1, the amount of fluorescence in real-time PCR showed a reduced increase. This is because when the micro-flow channel device for continuous-flow PCR was heated or cooled from the bottom of the device, temperature variations occurred in the cross-sectional direction of the serpentine channel, and the temperature thus could not be controlled to the desired temperature.

When the parallelly positioned straight-line flow paths of the serpentine channel have narrow intervals, the proportion of the flow channel area per unit area increases while the proportion of air increases; it was confirmed that the temperature was thus not sufficiently transmitted from the heat blocks to the surface of the chip. When the straight flow paths of the channel have short intervals therebetween, the thermal capacity is low around the paths, and heating is thus not sufficiently performed. Conversely, the same applies to the case where cooling is performed; the temperature was more efficiently changed as the flow paths have wider intervals.

As shown in FIG. 8, to maintain sufficient thermal capacity, the parallelly positioned straight-line flow paths of the serpentine channel have intervals of desirably 200 µm or more, preferably 400 µm or more, and most preferably 600 µm or more. In view of the above, when the micro-flow channel made of COP is used, flow paths having intervals comparable to the channel width are assumed to be effective to accurately control the temperature. It is revealed that the following are required for more efficient DNA amplification: ensuring the intervals between the parallelly positioned flow paths of the serpentine channel to maintain sufficient thermal capacity; and setting the aspect ratio of the cross-sectional surface of the flow channel to greater than ⅛ and less than 1 to prevent air bubble formation and to achieve stable flow. The technique for accurately controlling the temperature of the sample plug at a high speed serves as one feature of the present invention.

As the Examples of other genetic detection, the DNA fragment amplification by continuous-flow PCR, targeting the *Bacillus subtilis* gene, was analyzed. A CycleavePCR Bacteria Screening Kit produced by Takara Bio Inc. was used, and PCR reagents were prepared according to the kit instructions. The PCR reagents were each individually subjected to continuous-flow PCR. The prepared PCR reagent was simultaneously injected in the form of sample plugs (3 µL each) into the continuous-flow PCR microfluidic device. The reagent was introduced at a flow rate of 100 to 680 µL/min using a syringe pump (Model 11, produced by Harvard).

When a plurality of sample plugs are simultaneously introduced to perform continuous-flow PCR, and when two or more sample plugs are simultaneously present within a length equivalent to one cycle in the micro-flow channel, the flowing rhythm that is created by vapor pressure and that is required for the ideal thermal cycles is disturbed. Therefore, each sample plug was injected at time intervals sufficient for performing more than one cycle. In this manner, the rhythm of flow, such that each sample plug passes through the extension process at a reduced speed while it passes through the cooling process at an increased speed, is confirmed. Therefore, the number of sample plugs is not limited to 1 per one round of continuous-flow PCR, and it is possible to use a large amount of the sample solution.

Figure 9:
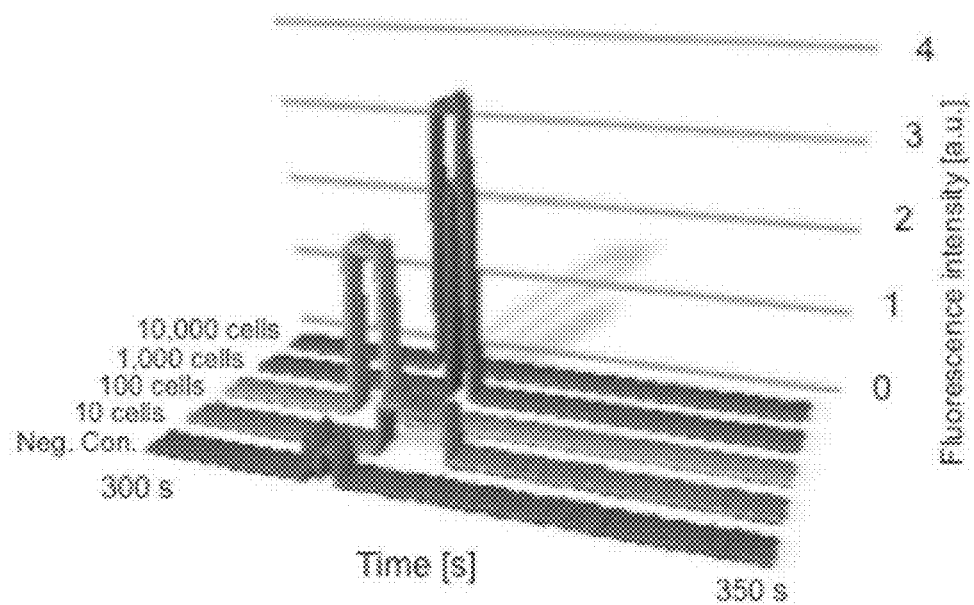
FIG. 9 is a graph showing fluorescence intensity detected at the outlet of the serpentine channel of the continuous-flow PCR microfluidic device, when a continuous-flow PCR for *Bacillus subtilis* gene was performed.
Figure 10:
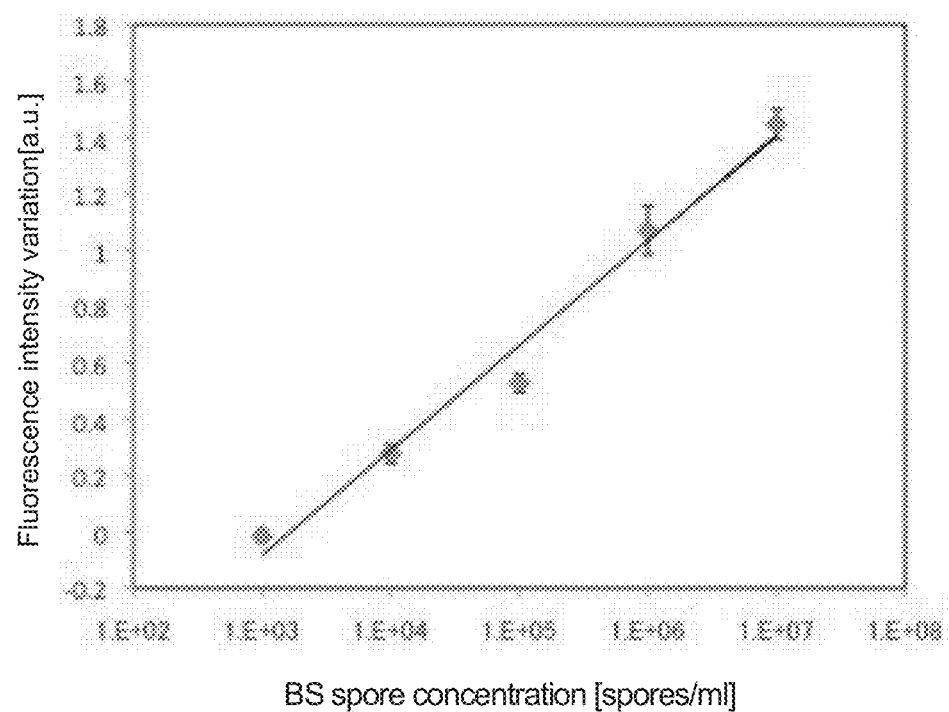
FIG. 10 is a graph showing the relationship between the amount of fluorescence measured in FIG. 9 and the amount of *Bacillus subtilis* mixed beforehand with the sample plugs.

A SELFOC fiber fluorescence detector was provided at a position of the serpentine channel near the outlet of the continuous-flow PCR microfluidic device, and the fluorescence intensity increased by continuous-flow PCR was measured in real time. As shown in FIG. 9, the obtained fluorescence intensity was varied proportional to the amount of the *Bacillus subtilis* mixed beforehand with the sample plug. The variance of the fluorescence intensity was quantified to produce a graph of a calibration curve, as shown in FIG. 10. The results show an excellent correlation between the obtained fluorescence intensity with the amount of the *Bacillus subtilis* in the reagent plug prepared as the PCR sample. This confirms that detection of the target gene is possible. Further, as shown in FIG. 9, it was confirmed that the process from the gene amplification to the detection can be very rapidly performed within about 6 minutes by using the continuous-flow PCR microfluidic device.

These analyses use a real-time PCR method, which confirms the DNA fragment amplification based on fluctuations of fluorescence intensity. However, the technique used in this specification is not limited to use in a real-time PCR, and may be used in a nucleic acid amplification technique using a PCR method including RT-PCR.

The above results clarify that the present invention can perform a PCR reaction at a very high speed.

EXPLANATION OF REFERENCE NUMERALS

1. PCR Sample Injection Tube
2. Serpentine Channel
3. Reservoir
4. Continuous-Flow PCR Microfluidic Device
5. Heater Block for Annealing
6. Heater Block for Extension Reaction
7. Heater Block for DNA Denaturation
8. Sample Plugs (Sample)

The invention claimed is:

1. A nucleic acid amplification method comprising the steps of:
    (a) supplying a PCR sample solution to a nucleic acid amplification device comprising a serpentine channel adapted to perform at least one PCR amplification cycle,
    wherein the serpentine channel comprises at least one DNA denaturation temperature zone corresponding to curved portions on a first side of the amplification device, at least one annealing temperature zone corresponding to curved portions on a second side of the amplification device, and at least one extension temperature zone positioned between the annealing temperature zone and the DNA denaturation temperature zone, and
    (b) introducing the PCR sample solution comprising at least first and second sample plugs into the serpentine channel by using a pump,
    wherein the first and second sample plugs are immediately adjacent to each other and are separated by a single partition of gas,
    wherein the first sample plug flows through a DNA denaturation temperature zone, an annealing temperature zone, and an extension temperature zone to perform a PCR amplification cycle, before the second sample plug is introduced into the serpentine channel
    wherein the first sample plug completes at least one PCR amplification cycle before the second sample plug begins a PCR amplification cycle, and
    wherein vapor pressure differences between the front and the back of the sample plug are used to ensure time for an enzymatic extension reaction by reducing flow speed from the annealing temperature zone to the DNA denaturation temperature zone during a heating process and by increasing flow speed from the DNA denaturation temperature zone to the annealing temperature zone during a cooling process, so that the PCR sample solution passes through the cooling process quicker than through the heating process.

2. The nucleic acid amplification method according to claim 1, wherein the PCR sample solution is supplied at a volume equal to or less than that of a straight-line portion of the serpentine channel.

3. The nucleic acid amplification method of claim 2, wherein the temperature control method for the sample plug comprises at least one of the temperature control methods below:
    (i) a method in which the temperature of an annealing heater for reducing temperature is cooled to 40° C. or less;
    (ii) a method in which parallelly positioned flow paths of the serpentine channel have intervals of 200 μm or more; and
    (iii) a method in which the cross-sectional aspect ratio of the serpentine channel is set to ⅛ or more and less than 1 to prevent air bubbles from being formed and to stabilize the flow.

4. The nucleic acid amplification method according to claim 2, wherein the method uses a thin membrane film in a chip for monitoring the temperature of the solution within the serpentine channel.

5. The nucleic acid amplification method of claim 4, wherein the temperature control method for the two or more sample plugs comprises at least one of the temperature control methods below:
    (i) a method in which the temperature of an annealing heater for reducing temperature is cooled to 40° C. or less;
    (ii) a method in which parallelly positioned flow paths of the serpentine channel have intervals of 200 μm or more; and
    (iii) a method in which the cross-sectional aspect ratio of the serpentine channel is set to ⅛ or more and less than 1 to prevent air bubbles from being formed and to stabilize the flow.

6. The nucleic acid amplification method according to claim 1, wherein the method uses a thin membrane film in a chip for monitoring the temperature of the solution within the serpentine channel.

7. The nucleic acid amplification method of claim 6, wherein the temperature control method for the sample plug comprises at least one of the temperature control methods below:
    (i) a method in which the temperature of an annealing heater for reducing temperature is cooled to 40° C. or less;
    (ii) a method in which parallelly positioned flow paths of the serpentine channel have intervals of 200 μm or more; and
    (iii) a method in which the cross-sectional aspect ratio of the serpentine channel is set to ⅛ or more and less than 1 to prevent air bubbles from being formed and to stabilize the flow.

8. The nucleic acid amplification method of claim 1, wherein the temperature control method for the sample plug comprises at least one of the temperature control methods below:
    (i) a method in which the temperature of an annealing heater for reducing temperature is cooled to 40° C. or less;
    (ii) a method in which parallelly positioned flow paths of the serpentine channel have intervals of 200 μm or more; and (iii) a method in which the cross-sectional aspect ratio of the serpentine channel is set to ⅛ or more and less than 1 to prevent air bubbles from being formed and to stabilize the flow.

* * * * *